United States Patent
Ferree et al.

(10) Patent No.: US 8,968,211 B2
(45) Date of Patent: Mar. 3, 2015

(54) ADJUSTABLE SAMPLE SIZE TISSUE SAMPLING DEVICE

(75) Inventors: Chris Ferree, Bloomington, IN (US); Casey Brown, Bedford, IN (US); Allen Hacker, Bloomington, IN (US); Danielle Joaquin, Tinley Park, IL (US); Anthony Melchiorri, Normal, IL (US); Torsten Schreiber, Indianapolis, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 146 days.

(21) Appl. No.: 13/293,162

(22) Filed: Nov. 10, 2011

(65) Prior Publication Data

US 2012/0179065 A1 Jul. 12, 2012

Related U.S. Application Data

(60) Provisional application No. 61/412,625, filed on Nov. 11, 2010.

(51) Int. Cl.
*A61B 10/00* (2006.01)
*A61B 10/02* (2006.01)

(52) U.S. Cl.
CPC ..... *A61B 10/0275* (2013.01); *A61B 2010/0093* (2013.01); *A61B 2010/0208* (2013.01)
USPC .......................................................... 600/564

(58) Field of Classification Search
CPC .................. A61B 10/0275; A61B 2010/0093; A61B 2010/0208
USPC ........................... 600/562–567; 606/167, 172
See application file for complete search history.

(56) References Cited

U.S. PATENT DOCUMENTS

| | | | | |
|---|---|---|---|---|
| 6,165,136 A | * | 12/2000 | Nishtala | 600/564 |
| 7,766,843 B2 | * | 8/2010 | Voegele | 600/567 |
| 2003/0163062 A1 | * | 8/2003 | Bauer | 600/567 |

* cited by examiner

*Primary Examiner* — Brian Szmal
(74) *Attorney, Agent, or Firm* — Woodard, Emhardt, Moriarty, McNett & Henry LLP

(57) ABSTRACT

Among other things, there is disclosed a biopsy needle capable of taking samples of varying size. In particular embodiments, a user selects one of a plurality of sample-size settings, which sets the needle to a particular cannula throw-length by moving an internal wall against which a spring engages. For a shorter throw, the wall is in a forward position and the cannula is retracted the smaller amount to compress the spring. For a longer throw, the wall is in a rearward position and the cannula is retracted a larger amount to compress the spring.

21 Claims, 6 Drawing Sheets

Fig. 4A  Fig. 4B

ADJUSTABLE SAMPLE SIZE TISSUE SAMPLING DEVICE

REFERENCE TO RELATED APPLICATION

This application claims the benefit of U.S. Provisional Patent Application No. 61/412,625, filed Nov. 11, 2010, which is hereby incorporated by reference.

The present disclosure concerns devices such as biopsy needles for obtaining a sample of human or animal tissue for testing or study. In particular, it concerns tissue-obtaining devices that allow a user to select from multiple sizes of sample, and methods for using such devices.

BACKGROUND

A variety of biopsy needles and similar devices for obtaining a tissue sample from a patient are known. Commonly, such devices include a thin needle or stylet that can be inserted into the skin of the patient near the location of tissue to be sampled, such as suspected malignancies or other tissue of interest. Once the distal end or other cutting portion of the needle or stylet is within the tissue of interest, a portion of the tissue is excised and captured. The needle or stylet is withdrawn with the tissue sample, which can be retrieved from the device and studied.

Such products have proven quite effective in obtaining tissue in a minimally-invasive manner and with minimal discomfort to the patient. Their lightweight, low-cost nature, combined with their ease of operation and reusability, make them excellent for sampling tissue that may present or indicate a health problem to the patient.

Most biopsy needles have only one sample size setting for each needle, and in many cases that setting is either for a length of sample of 10 mm or 20 mm. There are often cases where the physician or other clinician does not know which sample size is appropriate for the given patient. Having estimated that a 10 mm length of sample will do, a clinician might decide after a few such 10 mm samples that he or she may need to obtain more tissue to retrieve an adequate, testable sample. He or she would then have to dispose of the used 10-mm-sample biopsy needle and replace it with a new 20-mm-sample needle. This is inconvenient, and introduces additional discomfort to that patient and cost for supplies for the overall procedure.

Thus, if the tissue of interest is easily findable and of a size easily determined by the clinician, then he or she can choose a product that will provide the amount of tissue suggested by the patient's situation. However, in other cases there may be less certainty, meaning that the clinician may make an ultimately incorrect estimate of how much tissue to obtain, and therefore may have to use multiple biopsy devices to obtain samples of differing lengths or amounts. Further, hospitals, clinics and other health service providers must stock multiple versions of biopsy needles to be sure of having a product suited to particular needs. There remains a need for tissue sampling devices capable of obtaining varying amounts of tissue while maintaining the ease of use of the device.

SUMMARY

Among other things, there is disclosed an adjustable-throw biopsy needle that includes an elongated tissue-cutting member and a housing connected to the tissue-cutting member for propelling it forward into tissue when a tissue sample is desired. The housing includes a wall movable between at least a first and second position and a spring that engages the wall. The first position corresponds to a first throw-length of the tissue-cutting member with respect to the housing so that a first size of tissue sample can be obtained, and the second position corresponds to a second throw-length so that a second size of tissue sample can be obtained.

In some embodiments, the distance between the first and second positions of the wall can be approximately the same as the difference between the first and second throw-lengths. A slidable button can be placed on an outside surface of the housing, and the button may be connected to the wall so that sliding the button along the housing operates to move the wall between the first and second positions. The housing may include two finger holds lateral to a longitudinal axis of the cutting member, and the button may be between the finger holds so that the button and finger holds can be accessed by the fingers of one hand of a user. The housing may be provided with a first marking associated with the first position and first throw-length and a second marking associated with the second position and second throw-length, so that when the wall is in its first position, the first marking is indicated by the location of the button, and when the wall is in its second position, the second marking is indicated by the location of the button. The tissue-cutting member may be engaged to a carriage within the housing, and a catch may be positioned adjacent the carriage, so that the carriage is adapted to be held by the catch at first and second locations, with the first location associated with the first throw-length and the second location associated with the second throw-length. The first position of the wall can correspond to a maximum throw-length, and/or the second position of the wall can correspond to a minimum throw-length. The elongated tissue-cutting member may include a cannula having an internal lumen for making at least a part-cylindrical profile in tissue.

In other embodiments, an apparatus for sampling tissue includes a cannula having a longitudinal axis and defining a lumen along that axis, a stylet within the cannula's lumen so that the cannula and stylet are slidable with respect to each other, and a housing connected to the cannula and stylet. The housing includes a wall that is variably positionable within the housing along at least a direction parallel to the cannula's longitudinal axis, a movable carriage engaging the cannula, a spring engaged to the carriage and the movable wall, and an actuator operable to move the carriage to compress the spring against the wall. The housing is adapted to move the cannula a throw-length along the cannula's longitudinal axis, and varying the position of the wall corresponds with varying the throw-length of the cannula.

In particular embodiments, a slider is provided on the outside of the housing and connected to the wall, so that a user can move the wall within the housing by moving the slider along the housing. The wall may be positionable at at least first and second discrete positions, with the first discrete position corresponding to a first discrete length of tissue to be obtained and the second position corresponding to a second discrete length of tissue to be obtained. When the wall is at that first discrete position, the slider may be at a proximal-most position with respect to the housing, and when said wall is at the second discrete position, the slider can be at a distal-most position with respect to the housing. The first throw-length noted above is different from, e.g. smaller than, the second throw-length. The device can include a catch within the housing, so that the carriage and catch are adapted to interact so that the interaction allows the carriage to be maintained stationary in any of a plurality of locations within the housing. The distance between the first and second discrete positions is approximately the same as the difference between the first and second throw-lengths in some embodiments.

There is also disclosed an adjustable throw-length biopsy needle that includes a cannula and a housing connected to the cannula, with the housing including a wall movable between at least a first proximal position and a second distal position and a spring engaged with the wall. The spring is operable to propel the cannula forward with respect to the housing through tissue when a tissue sample is desired. The first proximal position corresponds to a first throw-length for the cannula to obtain a first size of tissue sample, and the second distal position corresponds to a second throw-length for the cannula to obtain a second size of tissue sample. A button can be provided that is slidable along the housing and connected to the wall, so that moving the button changes the position of the wall. When the wall is in the first proximal position, the button can reveal a marking on the housing indicating the first throw-length, and when the wall is in the second distal position, the button can reveal a marking on the housing indicating the second throw-length. A carriage movable within the housing and fixed to the cannula can be provided, and the carriage may be adapted to be held within the housing at a first location associated with the first throw-length and at a second location associated with the second throw-length.

The present disclosure resolves the limits of use of existing products by featuring an adjustable sample size for tissue sampling devices. In particular embodiments, a button, slider or similar device in the handle of a needle allows for quick and easy change in sample size. As an example, a neutral or default position of the button will provide a larger sample size (e.g. 20 millimeters in length). When the user locks the button in a forward or other secondary position, an internal wall or base moves forward or distally in the handle to a forward locked position. Such forward locking can partially compress a the spring in the handle and results in a smaller (e.g. 10 millimeter) sample size setting. To arm the system to a larger (e.g. 20 mm) setting, the clinician pulls back on the housing's trigger. One or more clicks are heard as the trigger passes position(s) associated with smaller setting(s), and when the trigger arrives at a position associated with a longer-throw setting, an additional click is heard indicating that the system is armed for the longer throw. The trigger would be retracted only to an earlier click (e.g. the first) when arming for a smaller setting. When changing from one setting to the other, an appropriate label (e.g. "10 MM" or "20 MM") will appear in some embodiments to inform the user what sample size is engaged.

BRIEF DESCRIPTION OF THE DRAWINGS

FIG. 4A is a close-up top plan view of part of the embodiment of FIG. 1 in a first state.

FIG. 4B is a close-up top plan view of part of the embodiment of FIG. 1 in a second state.

DESCRIPTION OF THE ILLUSTRATED EMBODIMENTS

Figure 1:
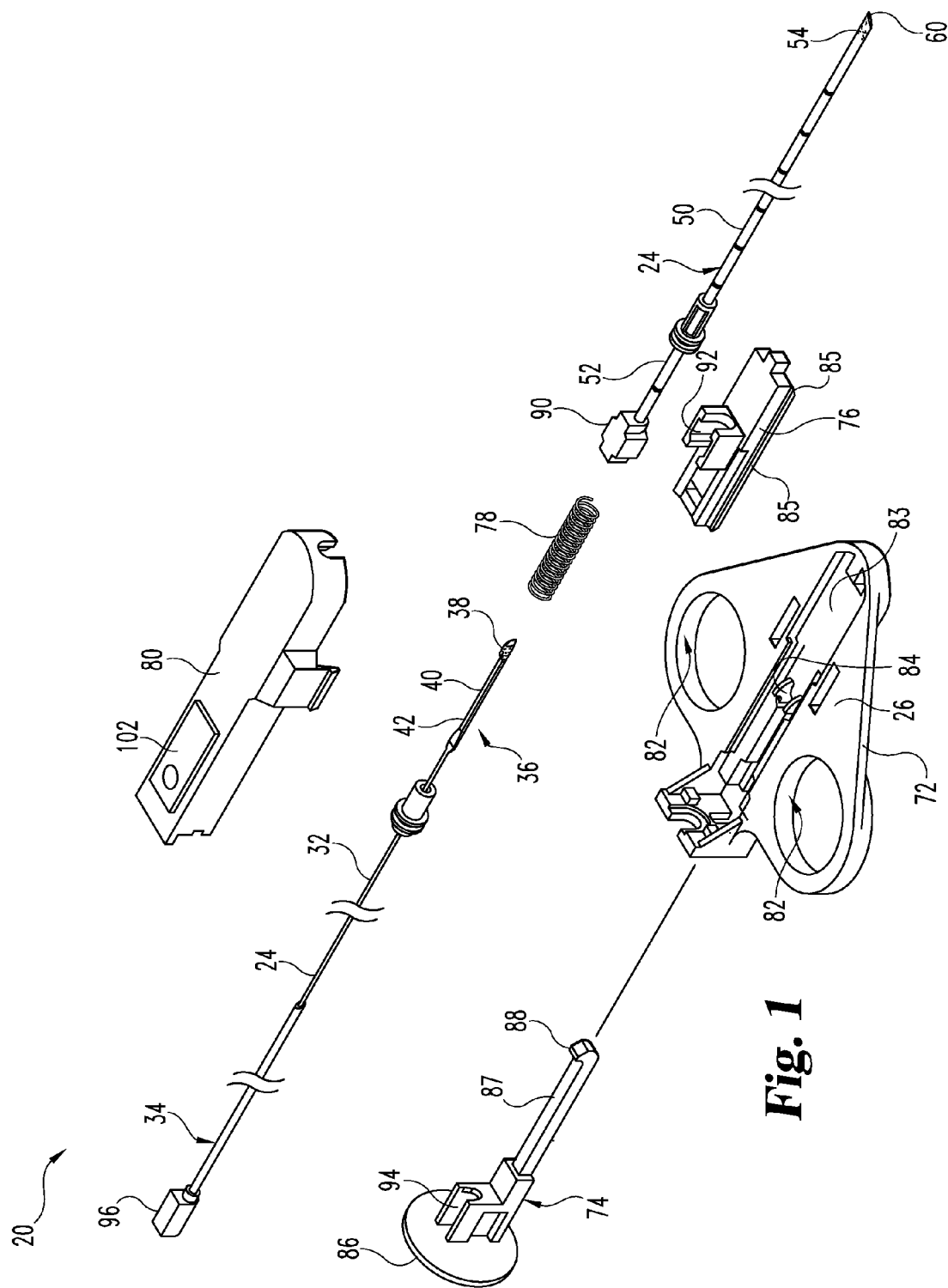
FIG. 1 is an exploded perspective view of an embodiment of a biopsy needle according to the present disclosure.
Figure 2:
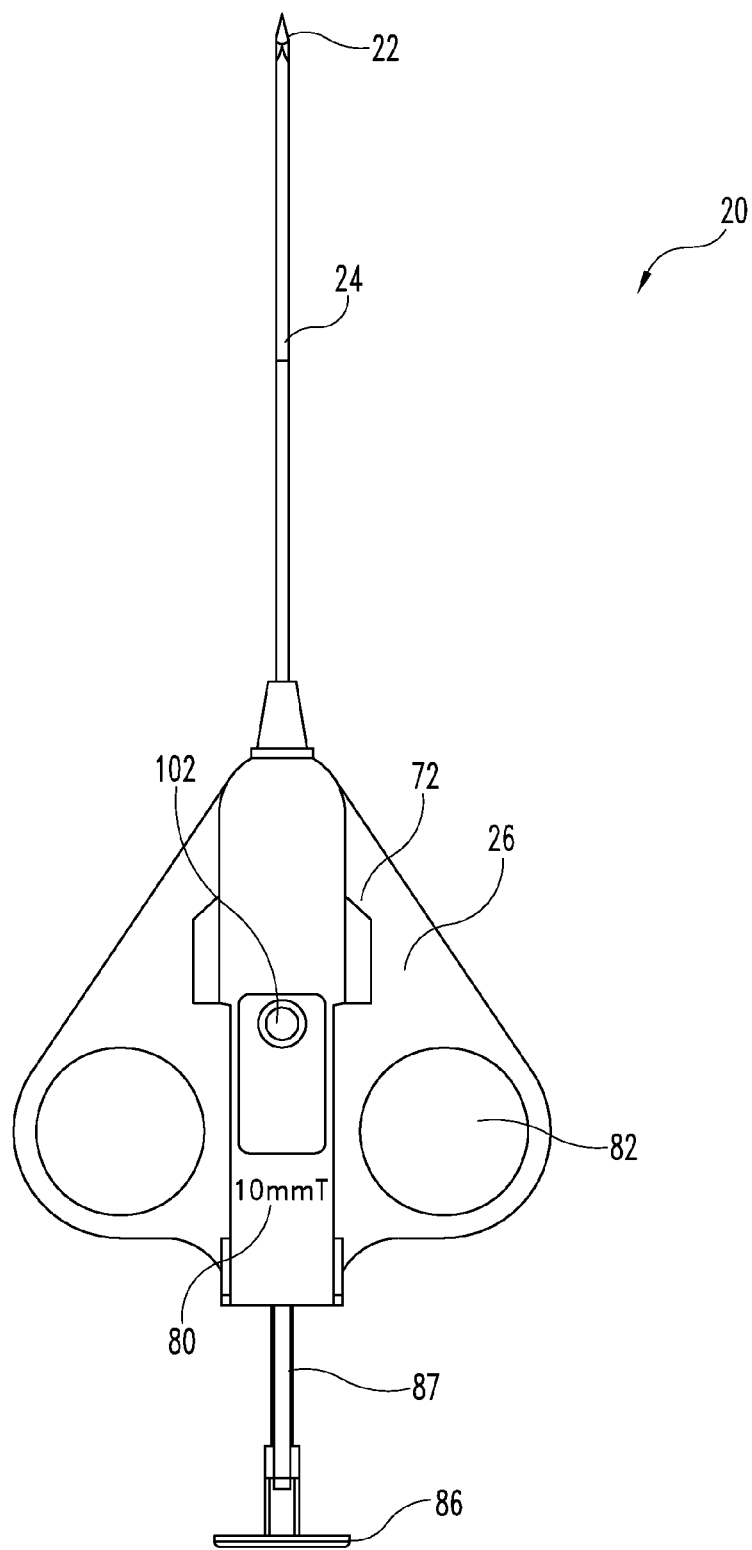
FIG. 2 is a top plan view of the embodiment of FIG. 1.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated embodiments, and such further applications of the principles of the disclosure as illustrated therein, being contemplated as would normally occur to one skilled in the art to which the disclosure relates.

Referring now generally to the drawings, there is shown an embodiment of a biopsy needle 20. Needle 20 includes an inner stylet 22, an outer cannula 24 and a handle 26. Both stylet 22 and cannula 24 are connected to and operable by handle 26 in this embodiment, as will be further explained below.

Stylet 22 is substantially cylindrical in the illustrated embodiment, having an elongated body 32 extending between a proximal end 34 and a distal end 36. Elongated body 32 is at least substantially circular in the illustrated embodiment for ease of use and manufacture. Proximal end 34 is connected to handle 26, as will be further discussed below. Distal end 36 may be sharpened, for example by grinding a surface 38 that is planar and oblique to the longitudinal axis of cannula 22.

Proximal of surface 38 there is formed in stylet 22 a notch 40. In the illustrated embodiment, notch 40 has a depth to a substantially flat inner surface 42 of approximately half of the diameter of stylet 22 or less, and an end surface 44 perpendicular to or forming an obtuse angle with surface 42. It will be understood that other embodiments of notch 40 can be of greater or lesser depths and/or can have end surface 44 oriented with an acute angle between surfaces 44 and 42. Notch 40 is provided so that tissue to be biopsied enters notch 40 and is cut off and contained in notch 40, as further discussed below.

Figure 3A:
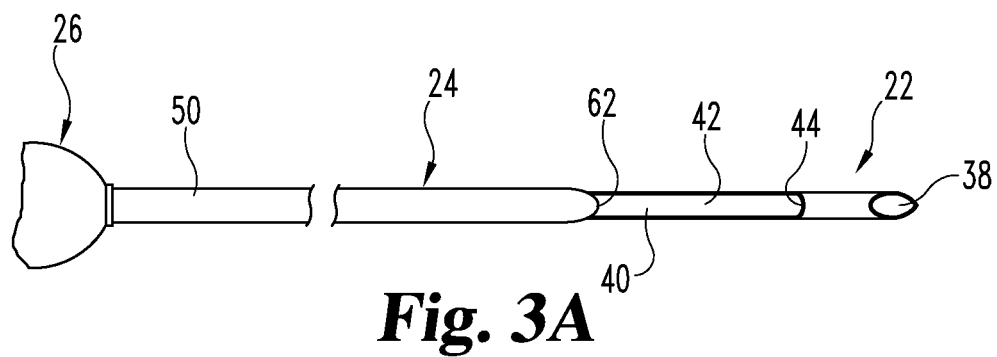
FIG. 3A is a partial top plan view of the embodiment of FIG. 1.
Figure 3B:
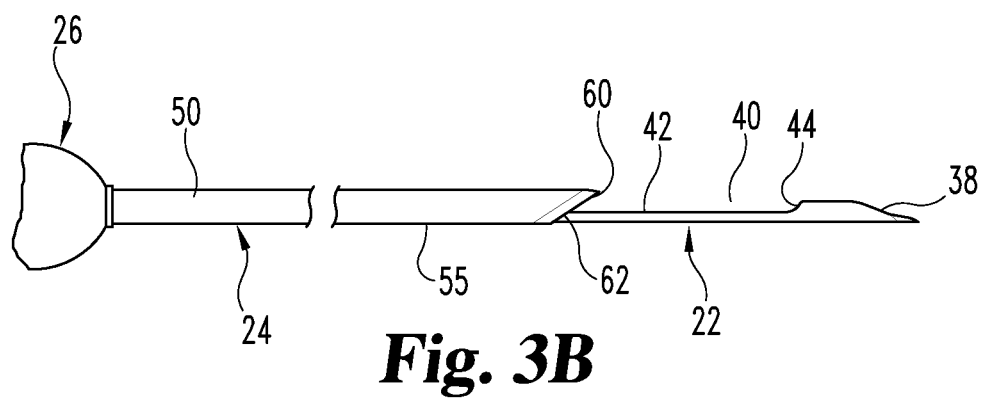
FIG. 3B is a partial side elevational view of the embodiment of FIG. 1.

The illustrated embodiment of cannula 24 is tubular, having an elongated body 50 extending between a proximal end 52 and a distal end 54. Elongated body 50 is of substantially the same cross-sectional shape as stylet 22 in some embodiments. Body 50 is at least substantially circular in the illustrated embodiment, having a cylindrical outer surface 55 and an inner cylindrical surface defining a lumen, for ease of use and manufacture. Proximal end 52 is connected to handle 26, as will be further discussed below. Tubular body 50 is cut obliquely at distal end 54 to form a surface 60 with one or more sharp edges 62. In the illustrated embodiment, an essentially planar oblique section is taken through cannula 24, so that end surface 60 and edge(s) 62 are formed. In the illustrated embodiment, the cut distal end 54 is beveled or otherwise shaped to an edge 62 so as to cut tissue as cannula 24 is advanced. In the illustrated embodiment, surface 60 is formed so that the relatively uppermost portion of cannula 24 (as seen in FIGS. 3A-3B and as generally inserted into the patient) is distal-most.

Handle 26 is connected to each of stylet 22 and cannula 24 at their respective proximal portions, so that stylet 22 is within cannula 24, and so that stylet 22 and cannula 24 are slidable with respect to each other. An example of structure usable as part of handle 26 is that currently used with QUICK-CORE® products sold by Cook Medical (Bloomington, Ind.). Embodiments of structure suitable for use in handle 26 are shown in U.S. Provisional Application No. 61/261,857, filed on Nov. 17, 2009, the entirety of which is incorporated herein by reference.

Handle 26, in the embodiment of FIG. 1, includes a housing 72, trigger or actuator 74, drive carriage 76, spring 78, and cover 80. Housing 72 includes finger holds 82 which are substantially circular in this embodiment, and a central channel 83 in which carriage 76 is slidable forward and backward (proximally and distally). A catch 84 is positioned in channel 83 for holding carriage 76, and carriage 76 includes at least two pawl surfaces 85 (e.g. teeth, prongs and/or edges of grooves) on an underside to interact with catch 84. Actuator 74 includes a grip or pad 86 positioned at its proximal end in this embodiment, and a distally-extending finger 87 with and end boss 88 that can engage carriage 76 to draw it proximally. Carriage 76 is coupled to a proximal portion of cannula 24, e.g. by inserting a hub 90 or other portion of cannula 24 into an opening 92 (which may be complementary to hub 90 or other portion of cannula 24) of carriage 76, with cannula 24 extending from carriage 76. In this embodiment, an opening 94 in the structure of actuator 74 is sized and configured to accommodate a portion or hub 96 of stylet 22. Spring 78 is provided adjacent to carriage 76 to propel carriage 76 and cannula 24 forward, as discussed further below. Cover 80 fits onto housing 72, covering and protecting spring 78 and sliding engagement between drive carriage 76 and housing 72 from debris and interference.

In addition, handle 26 includes an adjustable wall or surface 100 engaging spring 78 and against which spring 78 is compressed. Wall 100 is in a proximal location of handle 26 in this embodiment, and is connected to a button or slider 102 that is on the exterior of housing 72, e.g. on top of cover 80. In the illustrated embodiment, wall 100 is fixed or monolithic with slider 102 so that wall 100 is at least approximately perpendicular to slider 102 and to the longitudinal axis (direction of travel) of cannula 24. Wall 100 and/or slider 102 have a frictional fit with the sides of channel 83 in a particular embodiment so that wall 100 occupies and/or is held in particular positions or at particular locations (which may be determined by the possible extent of movement of button 102 along cover 80) within housing 72. In some embodiments, the user may hold slider 102 in place in order to maintain wall 100 in a desired location. It will be understood that cover 80 may include a slot or other opening to allow for the connection of button 102 and wall 100.

Figure 5A:
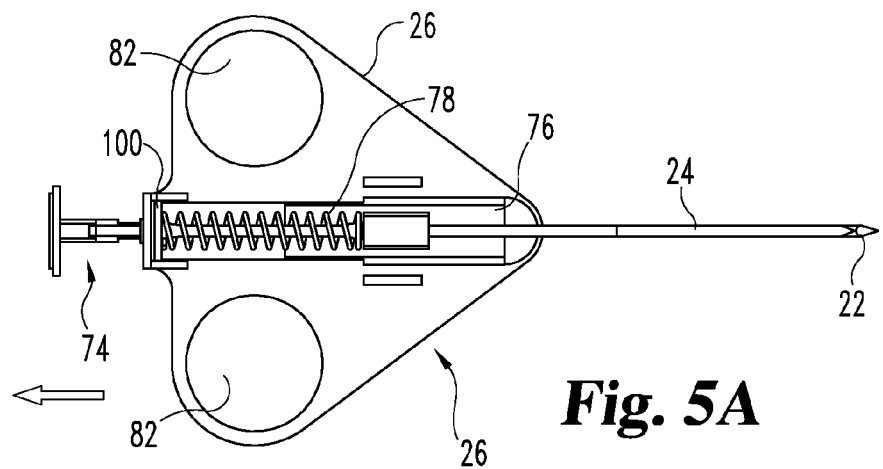
FIG. 5A is a top plan view of part of the embodiment of FIG. 1 in an initial state.
Figure 5B:
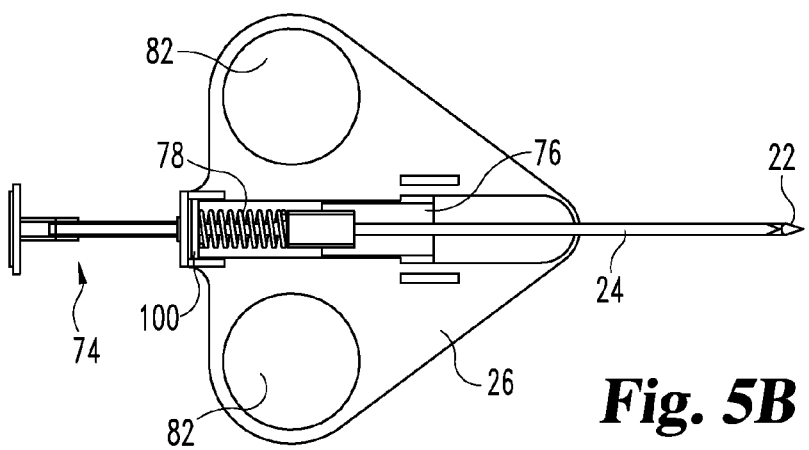
FIG. 5B is a top plan view of part of the embodiment of FIG. 1 in a cocked state.
Figure 5C:
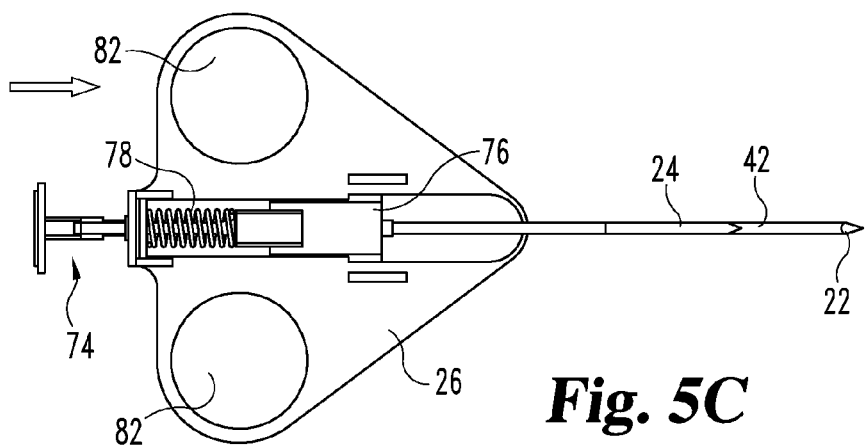
FIG. 5C is a top plan view of part of the embodiment of FIG. 1 in a primed or ready-to-fire state.
Figure 6A:
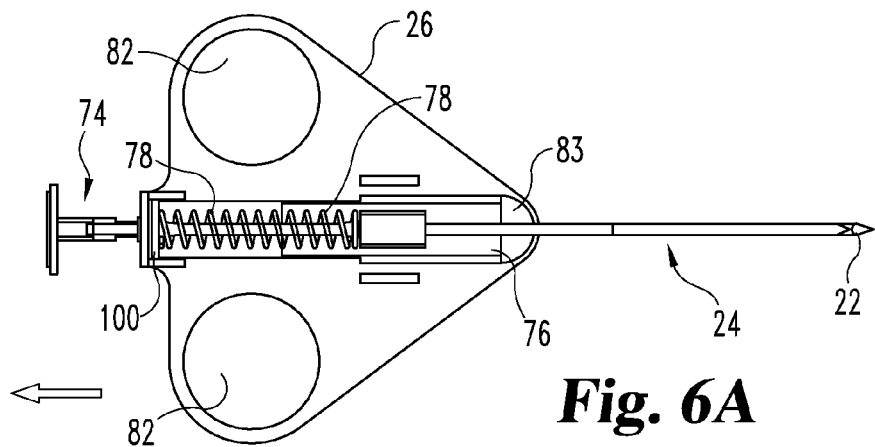
FIG. 6A is a top plan view of part of the embodiment of FIG. 1 in an initial state.
Figure 6B:
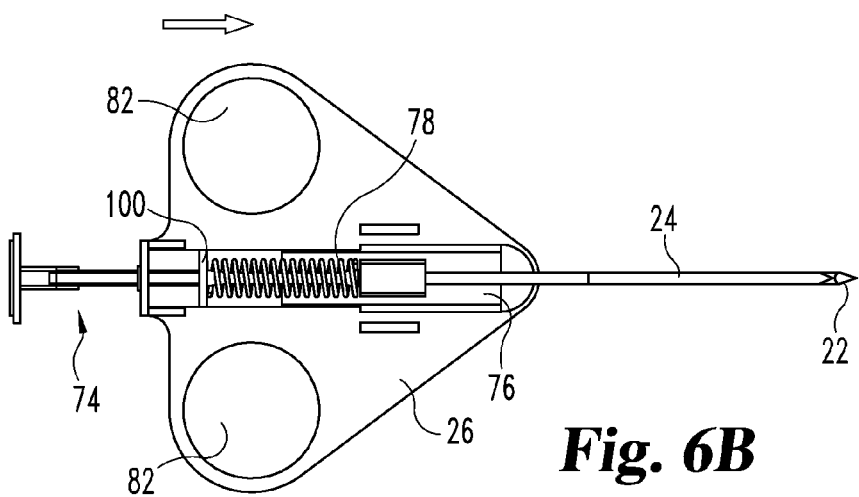
FIG. 6B is a top plan view of part of the embodiment of FIG. 1 in a cocked state.
Figure 6C:
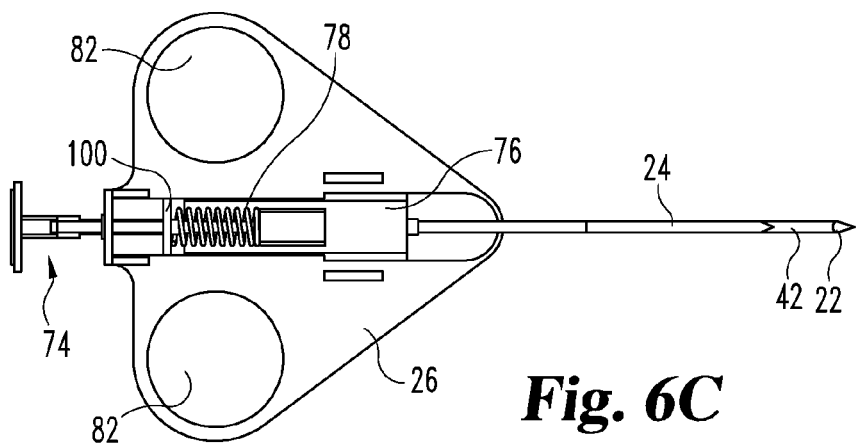
FIG. 6C is a top plan view of part of the embodiment of FIG. 1 in a primed or ready-to-fire state.

In a particular embodiment wall 100 (with button 102) has a first position against or adjacent the proximal-most internal wall of housing 72 (e.g. FIGS. 5A-5C), and a second position a discrete distance distal of the first position (e.g. FIGS. 6B-6C). The first position, in this embodiment, corresponds to a largest-possible (or larger) throw of cannula 24 and therefore a larger sample size, e.g. 20 millimeters. The second position corresponds to a smaller throw and sample size, e.g. 10 millimeters. In those dimensions, the second position is 10 millimeters forward of the first position. In a particular embodiment, the first position (the larger throw) is a default position, and the second position can only be achieved by the user's action in moving slider 102.

Figure 4C:
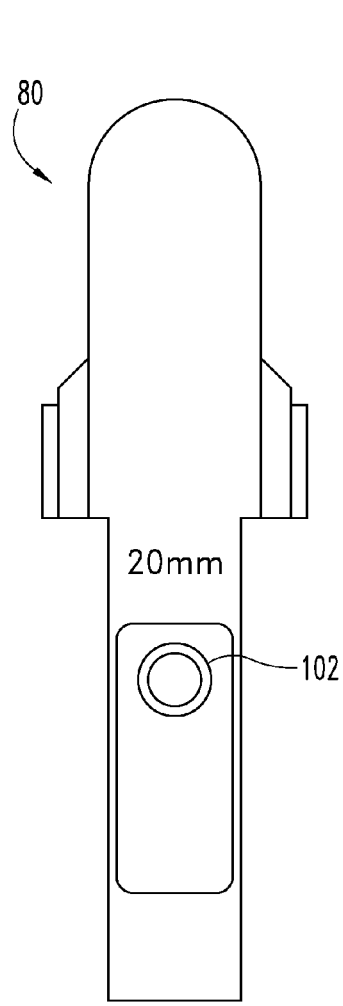
FIG. 4C is a part cross-sectional view of the part shown in FIG. 4B, taken along the lines 4C-4C in FIG. 4b and viewed in the direction of the arrows.
Figure 4C:
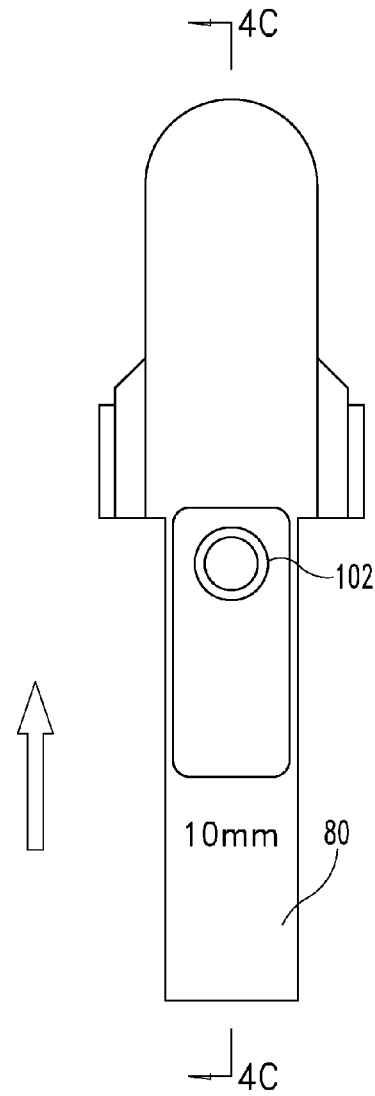
Figure 4C:
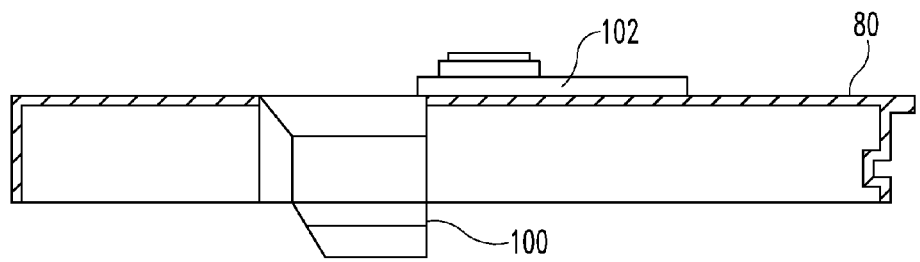

Button 102 is movable along housing 72 to move wall 100 between the two positions. Housing 72 includes indicators as to which position wall 100 is in and/or how large of a sample needle 20 is set for. In a particular embodiment, shown in FIGS. 4A and 4B, the legends "10 MM" and "20 MM" are placed on housing 72 (e.g. by label, imprinting or other means) so that one of the legends is uncovered in each position. That is, when button 102 is in a location on housing 72 corresponding to the first position or larger sample (e.g. FIG. 4A), the legend "20 MM" is uncovered, indicating that wall 100 (and thus needle 20) is set for a 20 millimeter throw and 20 millimeter sample length. When button or panel 102 is in a location on housing 72 corresponding to the second position or smaller sample (e.g. FIG. 4B), the legend "10 MM" is uncovered, indicating that wall 100 (and needle 20) is set for a 10 millimeter throw and 10 millimeter sample length (e.g. the distance D noted in FIG. 6C). It will be understood that markings may be provided on housing 72 along the path of button or panel 102 (e.g. score lines with numeric or other size indicators) as another way to show the size of sample needle 20 is set for.

Carriage 76 has two pawl surfaces 85 in this embodiment, each corresponding to a respective one of the throw-lengths or sample sizes. For example, in a needle having 10 and 20 millimeter sample capability, carriage 76 would have a pawl surface 85 that is near or at the front of carriage 76, and another that is 10 millimeters back from the other. It will be understood that more than two positions for wall 100 (and button 102) and/or additional pawl surfaces 85 under carriage 76, with corresponding sample sizes, can be provided. With additional positions for wall 100, additional flexibility to the clinician in deciding what sample size to obtain is provided.

When assembled, handle 26 is cocked by pulling actuator 74 (e.g. via grip 86) out or away from housing 72. With boss 88 of actuator 74 engaging carriage 76, when actuator 74 is pulled out from housing 72, carriage 76 is pulled backward (proximally) within channel 83, compressing spring 78 between wall 100 and carriage 76. Catch 84 engages the underside of carriage 76 (e.g. pawl surfaces 85) to maintain a cocked position. Pulling grip 86 proximally moves both cannula 24 and stylet 22 together, maintaining their respective tips at approximately the same location.

As noted above, the illustrated embodiment of needle 20 has two settings corresponding to two sample sizes or throw-lengths, exemplified as 10 millimeter and 20 millimeter sample sizes. If a larger (e.g. 20 millimeter) sample is desired, button 102 is at a first (more proximal) position so that wall 100 engages or is adjacent to the proximal end of channel 83 (e.g., as shown in FIG. 5A-5C). Such a first or more proximal position may be the default position or initial state of button 102 and/or wall 100, so that no change or adjustment to wall 100 is needed if a larger sample is desired. To cock needle 20, actuator 74 is pulled backward (proximally) against the bias of spring 78 past a first click (catch 84 passing the first of pawl surfaces 85 on carriage 76) to a second click corresponding to catch 84 moving over and being held by the second of pawl surfaces 85 on carriage 76 (e.g. FIG. 5B). If the smaller sample size is desired, button 102 is at a second or more distal position so that wall 100 is separated from the proximal end of handle 26 by a distance (e.g. FIGS. 6B-6C). In this example, the separation is approximately 10 millimeters, i.e. the difference between available throw-lengths or sample sizes. Button 102 and wall 100 are held in that position so that spring 78 can be compressed against wall 100, and moving button 102 forward (distally) to a second position can operate to partially compress spring 78 in some embodiments. Once button 102 is in place, grip 86 is pulled backward (proximally) to the first click, indicating that catch 84 has moved over and is held by the first of pawl surfaces 85 of carriage 76 (e.g. FIG. 6B).

Spring 78 is compressed by the same or substantially the same amount for both desired sizes of sample in the present embodiment. That is, in the illustrated embodiment when wall 100 is at its proximal-most, carriage 76 is retracted a greater amount so that the distance between them (occupied by spring 78) is the same as when wall 100 is distal-most and carriage 76 is retracted a lesser amount. The principal differences between the discrete sizes noted in the illustrated embodiment are (1) that the base or wall 100 against which spring 78 is compressed is in a different place, and (2) that the carriage 76 is retracted (by pulling grip 86) a different amount. In each case for this embodiment, the distance between carriage 76 and wall 100 when needle 20 is cocked and ready to fire is approximately the same.

Once needle 20 is cocked, the user pushes grip 86 to move actuator 74 forward a distance sufficient to prime needle 20 by moving notch 40 of stylet 22 out of the distal end of cannula 24 (e.g. FIGS. 5C, 6C). Such forward movement of actuator 74 moves stylet 22 because of the connection of stylet 22 with actuator 74, but does not move carriage 76 and cannula 24 because boss 88 does not push carriage 76. When notch 40 is exposed, further forward movement of actuator 74 (and stylet 22) is impeded by carriage 76 and catch 84. As will be explained further below, this priming step is performed once needle 20 is inserted into the patient so that the distal ends of stylet 22 and cannula 24 are in or almost in the tissue to be sampled, and operates to allow tissue into notch 40.

Needle 20 is fired to capture tissue within notch 40 by releasing spring 78 to move cannula 24 quickly forward. Pushing grip 86 further toward housing 72 pushes the pawl surface(s) of carriage 76 that had held carriage 76 over catch 84, releasing the hold on spring 78 and allowing its stored energy to be used to push drive carriage 76, in turn thrusting cannula 24 over notch 40 of stylet 22. In situations in which needle 20 is set for a larger throw, the energy stored in spring 78 is sufficient to propel carriage 76 over any intermediate projection(s) 85 and cannula 24 through tissue. That is, where there are only two settings, as in the illustrated embodiment, and a larger setting requires two clicks in cocking as noted above, pressing actuator 74 to overcome one pawl surface 85 releases sufficient energy from spring 78 to propel carriage 76 over the other pawl surface 85.

As described in greater detail below, firing handle 26 propels cannula 24 over stylet 22 to sever and trap tissue within notch 40 of stylet 22. The illustrated embodiment of needle 20 is a single action biopsy device which is effective when used to obtain tissue samples.

Handle 26 permits a cocking step that prepares the handle to fire cannula 24 over and along stylet 22 (e.g. FIGS. 5B, 6B), an insertion step in which the relatively positioned stylet 22 and cannula 24 are inserted into the body, and a firing step in which cannula 24 is released to move forward rapidly (pushed forward by spring 78) over stylet 22 and return to or toward the unstressed state. The cocking step is performed by holding finger holds 82 and pulling back on actuator 74 until it clicks as discussed above. Inserting needle 20 is accomplished while holding finger holds 82 by forcing handle 26 (and connected stylet 22 and cannula 24) forward into the body. If the cocking step precedes the insertion into the body, then handle 26 should be pushed forward without pushing on actuator 74. Pushing actuator 74 forward gently following insertion moves notch 40 out from cannula 24, and allows tissue into notch 40. Firing cannula 24 is accomplished by pushing forward actuator 74 to overcome the cocked state, and may be accomplished by the same hand that holds finger grips 82 in this embodiment. The firing propels cannula 24 over stylet 22 and through tissue, trapping a length of tissue in notch 40. The steps noted above may be applied in a different order, as may be indicated by the clinical situation.

Cannula 24 and stylet 22 are slidable with respect to each other, as indicated above. Stylet 22 extends from its connection with handle 26 through the lumen of outer cannula 24. In a particular embodiment, the outer diameter of inner cannula 22 is approximately the same as the inner diameter of outer cannula 24, so that there is little play or space between cannulas 22 and 24, yet they can move smoothly with respect to each other. Stylet 22 and cannula 24 have a first relative position (e.g. FIGS. 5A, 6A) which is seen before cocking or after firing needle 20. In that first relative position, stylet 22 and cannula 24 are approximately coextensive in the illustrated embodiment, i.e. distal ends of stylet 22 and cannula 24 are at approximately the same location.

The use of needle 20 will now be described in the context of obtaining a sample of soft tissue for testing purposes. It will be understood that methods for obtaining samples of other tissues or for other purposes are also contemplated.

The surgeon or other medical professional first determines a location in a patient, with its depth under the skin, from which a tissue sample is desired. In one embodiment, stylet 22 and cannula 24 of needle 20 are initially in the relative position indicated in the example of FIGS. 5A and 6A. The user chooses a throw-length according to the length of sample he or she believes is needed. The illustrated embodiment provides a choice between two throw lengths, 10 millimeters and 20 millimeters, and so the user chooses between them. In the illustrated embodiment, if the user chooses the shorter throw length, he or she moves button 102 distally (as explained above), and the label "10 MM" is uncovered. If the user chooses the longer throw length, the user need do nothing if the longer throw length is the default condition of button 102, or if not the user moves button 102 proximally (as explained above) to expose the label "20 MM." The user then cocks needle 20, as noted above, by pulling actuator 74 of handle 26 until at least one pawl surface 85 of carriage 76 catches on catch 84. In the cocked state, in this embodiment, stylet 22 and cannula 24 are in a relative position exemplified in FIGS. 5B and 6B, with ends of stylet 22 and cannula 24 substantially coinciding and retracted from the position of FIGS. 5A and 6A.

In that state, the user places distal ends 36 and/or 54 of stylet 22 and/or cannula 24 against the skin at a place proximate to the desired location, and inserts needle 20. Needle 20 forces a path through the skin and subcutaneous tissue to a point in or just before the location from which a sample is to be taken. The path size and shape is determined by the outer configuration of cannula 24. In embodiments in which cannula 24 is very thin, the path is not substantially larger than the outer diameter of stylet 22, reducing discomfort from the biopsy procedure.

Actuator 74 is then moved forward an amount permitted by handle 26 until further movement is obstructed. That advancement moves notch 40 beyond cannula 24, as noted above, to face tissue to be sampled (e.g. FIGS. 5C, 6C). Recoil of such tissue results in tissue entering notch 40. When stylet 22 is fully-advanced, with tissue in notch 40, the user fires cannula 24 forward by pressing actuator 74 to force it beyond catch 84. Once past catch 84, spring 78 (which is pressed against wall 100) releases its energy to push cannula 24 forward through the chosen throw-length. As cannula 24 moves forward, its forward edge 62 cuts through tissue, trapping it in notch 40 of stylet 22.

After firing, with stylet 22 and cannula 24 back in the extended relative position indicated in FIGS. 5A and 6A, needle 20 is withdrawn. Once needle 20 is withdrawn, the tissue sample is removed by cocking and priming needle 20, as indicated above, to expose notch 40 and the tissue within it. The tissue can be extracted using a forceps or other tool, or in some embodiments by inverting notch 40 and allowing the tissue to drop out of notch 40 into a specimen dish or other container. If the user determines that additional sample(s) are needed, then the procedure above can be repeated to obtain such samples.

In particular, it is noted that there may be occasions in which the user chooses a throw-length for needle 20, uses needle 20 to obtain a sample, and then determines that the obtained sample is too long (e.g. it obtains a significant amount of tissue not of interest) or too short (e.g. the sample does not extend to the end of the tissue region of interest. In such cases, the user changes the setting of button 102 (with wall 100) to another throw-length, and repeats the sampling process to obtain a new sample of the new size.

The illustrated embodiment has two throw-length settings, exemplified as 10 and 20 millimeters. It will be understood that other throw lengths can be used in place of one or both of such lengths. Further, it will be understood that three or more throw-length settings may be provided in needle 20. For example, a third or additional pawl surfaces 85 on carriage 76 and/or additional set positions for button 102 and wall 100 may also be provided so as to allow additional throw-length settings.

As used herein, the term "throw length" is intended to mean the distance a part is moved forward in use of the device. For example, a 10 millimeter throw length for the embodiments noted above indicates that cannula 24 is moved or forced forward a distance of about 10 millimeters with respect to housing 26 and/or the patient with whom needle 20 is used.

In the illustrated embodiment, stylet 22 has a close fit with cannula 24 within its lumen 58, and the two are slidable with respect to each other. By having both a "close fit" and slidability, it is meant that there is no substantial separation or gap between stylet 22 and cannula 24, as by a boss or flange. As seen in the embodiments in the drawings, stylet 22 and cannula 24 have a close and slidable fit at least along their respective distal ends, and in some embodiments that close and slidable fit extends along all or substantially all of one or both of their respective lengths. Such a configuration minimizes the external size of a needle needed to obtain a particular amount of tissue.

Such tissue sampling devices reduce the inventory that must be kept by hospitals, clinics or other medical-care facilities, freeing shelf space available to clinicians. Currently, a clinician needs multiple editions of each biopsy device (e.g. a 10 mm and 20 mm version) for each gage and length of stylet and cannula combination, and for each patient. Combining multiple settings into one system will cut the product shelf volume, and the number of products to be available for each patient, to a fraction.

While the embodiments have been illustrated and described in detail in the drawings and foregoing description, the same is to be considered as illustrative and not restrictive in character, it being understood that only preferred embodiments have been shown and described and that all changes and modifications that come within the spirit of the claims are desired to be protected.

What is claimed is:

1. An adjustable-throw biopsy needle, comprising:
   an elongated tissue-cutting member;
   a housing connected to said tissue-cutting member for propelling said tissue-cutting member forward into tissue when a tissue sample is desired, said housing including a wall within said housing movable between at least a first and second position and a spring that engages said wall,
   wherein said first position corresponds to a first throw-length of said tissue-cutting member with respect to said housing whereby a first size of tissue sample can be obtained, and said second position corresponds to a second throw-length of said tissue-cutting member with respect to said housing whereby a second size of tissue sample can be obtained.

2. The biopsy needle of claim 1, wherein the distance between said first and second positions of said wall is the same as the difference between said first and second throw-lengths.

3. The biopsy needle of claim 1, further comprising a slidable button on an outside surface of said housing, said button connected to said wall, wherein sliding said button along said housing operates to move said wall between said first and second positions.

4. The biopsy needle of claim 3, wherein said housing includes two finger holds lateral to a longitudinal axis of said cutting member, and said button is between said finger holds whereby said button and said finger holds are adapted to be accessed by the fingers of one hand of a user.

5. The biopsy needle of claim 3, wherein said housing includes a first marking associated with said first position and first throw-length and a second marking associated with said second position and second throw-length, so that when said wall is in said first position, said first marking is indicated by the location of said button, and when said wall is in said second position, said second marking is indicated by the location of said button.

6. The biopsy needle of claim 1, wherein said tissue-cutting member is engaged to a carriage within said housing, and wherein a catch is positioned adjacent said carriage, and wherein said carriage is adapted to be held by said catch at first and second locations, said first location associated with said first throw-length and said second location associated with said second throw-length.

7. The biopsy needle of claim 2, wherein said first position corresponds to a maximum throw-length.

8. The biopsy needle of claim 2, wherein said second position corresponds to a minimum throw-length.

9. The biopsy needle of claim 1, wherein said elongated tissue-cutting member includes a cannula having an internal lumen for making at least a part-cylindrical profile in tissue.

10. An apparatus for sampling tissue, comprising:
    a cannula having a longitudinal axis and defining a lumen along said axis;
    a stylet within the lumen of said cannula, wherein said cannula and said stylet are slidable with respect to each other; and
    a housing connected to said cannula and said stylet, said housing including a wall that is variably positionable within said housing along at least a direction parallel to the longitudinal axis of said cannula, a movable carriage engaging said cannula, a spring engaged to said carriage and said wall, and an actuator operable to move said carriage to compress said spring against said wall;
    wherein said housing is adapted to move said cannula a throw-length along said longitudinal axis, and wherein the position of said wall corresponds with the throw-length of said cannula.

11. The apparatus of claim 10, further comprising a slider on the outside of said housing and connected to said wall, whereby said wall is configured to move within said housing by moving said slider along said housing.

12. The apparatus of claim 11, wherein said wall is positionable at at least first and second discrete positions, said first discrete position corresponding to a first discrete length of tissue to be obtained and said second position corresponding to a second discrete length of tissue to be obtained.

13. The apparatus of claim 12, wherein when said wall is at said first discrete position, said slider is at a proximal-most position with respect to said housing, and when said wall is at said second discrete position, said slider is at a distal-most position with respect to said housing.

14. The apparatus of claim 13, wherein said first throw-length is smaller than said second throw-length.

15. The apparatus of claim 10, further comprising a catch within said housing, wherein said carriage and said catch are adapted to interact so that said interaction allows said carriage to be maintained stationary in any of a plurality of locations within said housing.

16. The apparatus of claim 12, wherein the distance between said first and second discrete positions is the same as the difference between the first and second throw-lengths.

17. An adjustable throw-length biopsy needle, comprising:
a cannula;
a housing connected to said cannula, said housing including a wall within said housing movable between at least a first proximal position and a second distal position and a spring engaged with said wall, said spring operable to propel said cannula forward with respect to said housing through tissue when a tissue sample is desired,
wherein said first proximal position corresponds to a first throw-length for said cannula whereby a first size of tissue sample can be obtained, and said second distal position corresponds to a second throw-length for said cannula whereby a second size of tissue sample can be obtained.

18. The biopsy needle of claim 17, further comprising a button slidable along said housing and connected to said wall, wherein said button is configured so that moving said button changes the position of said wall.

19. The biopsy needle of claim 18, wherein when said wall is in said first proximal position, said button is configured to reveal a marking on said housing indicating said first throw-length, and when said wall is in said second distal position, said button is configured to reveal a marking on said housing indicating said second throw-length.

20. The biopsy needle of claim 17, further comprising a carriage movable within said housing and fixed to said cannula, said carriage adapted to be held within said housing at a first location associated with said first throw-length and at a second location associated with said second throw-length.

21. A method comprising:
providing the biopsy needle of claim 1;
selecting a desired sample size and verifying that the wall is in position to provide the selected sample size;
inserting said needle into a patient; and
firing said needle so that the cannula moves forward with respect to the patient to obtain the selected size of sample.

\* \* \* \* \*